US012691175B2

(12) United States Patent
Chen et al.

(10) Patent No.: US 12,691,175 B2
(45) Date of Patent: Jul. 28, 2026

(54) DRUG TRANSDERMAL DELIVERY SYSTEM

(71) Applicant: Xiamen University, Xiamen (CN)

(72) Inventors: Ming Chen, Xiamen (CN); Haojie Zhai, Xiamen (CN)

(73) Assignee: Xiamen University, Xiamen (CN)

( * ) Notice: Subject to any disclaimer, the term of this patent is extended or adjusted under 35 U.S.C. 154(b) by 954 days.

(21) Appl. No.: 17/572,560

(22) Filed: Jan. 10, 2022

(65) Prior Publication Data

US 2022/0249668 A1 Aug. 11, 2022

Related U.S. Application Data

(63) Continuation of application No. PCT/CN2020/101041, filed on Jul. 9, 2020.

(30) Foreign Application Priority Data

Jul. 10, 2019 (CN) .......................... 201910619867.8

(51) Int. Cl.
| *A61K 41/00* | (2020.01) |
| *A61K 9/00* | (2006.01) |
| *A61K 47/46* | (2006.01) |

(52) U.S. Cl.
CPC ........ *A61K 41/0047* (2013.01); *A61K 9/0021* (2013.01); *A61K 47/46* (2013.01)

(58) Field of Classification Search
CPC ............................ A61K 41/0047; A61K 47/46
See application file for complete search history.

(56) References Cited

U.S. PATENT DOCUMENTS

2011/0040236 A1 2/2011 Isaacs et al.

FOREIGN PATENT DOCUMENTS

| CN | 104117138 | A | 10/2014 | |
| CN | 105858669 | A | 8/2016 | |
| CN | 105999535 | * | 10/2016 | ............ A61M 37/00 |
| CN | 105999535 | A | 10/2016 | |
| CN | 106310460 | A | 1/2017 | |
| CN | 106413798 | A | 2/2017 | |
| CN | 108136166 | A | 6/2018 | |
| CN | 108697639 | A | 10/2018 | |
| CN | 108744261 | A | 11/2018 | |
| CN | 110613892 | A | 12/2019 | |
| WO | 2008054362 | A2 | 5/2008 | |
| WO | 2016141144 | A1 | 9/2016 | |
| WO | 2017079760 | A1 | 5/2017 | |

OTHER PUBLICATIONS

Mitragotri, S. et al., Low-frequency sonophoresis: A noninvasive method of drug delivery and diagnostics, 2000, Biotechnology Progress, vol. 16, 488-492 (Year: 2000).*
Zhang, S. et al., Skin delivery of hydrophilic biomacromolecules using marine sponge spicules, Aug. 1, 2017, Molecular Pharmaceutics, vol. 14, 3188-3200 (Year: 2017).*
Petchsangsai, M. et al., The combination of microneedles with electroporation and sonophoresis to enhance hydrophilic macromolecule skin penetration, Biol. Pharm. Bull., vol. 37, 1373-1382 (Year: 2014).*
Han, T. et al., Permeability enhancement for transdermal delivery of large molecule using low-frequency sonophoresis combined with microneedles, Pharm, Drug Deliv., and Pharm. Tech., 2013, vol. 102, 3614-3622 (Year: 2013).*
International Search Report and English Translation cited in PCT/CN2020/101041 mailed Sep. 28, 2020, 10 pages.
Written Opinion cited in PCT/CN2020/101041 mailed Sep. 28, 2020, 5 pages.
Zhang, et al., "Skin delivery of hyaluronic acid by the combined use of sponge spicules and flexible liposomes", The Royal Society of Chemistry 2019, rsc.li/biomaterials-science, vol. 7, No. 4, Apr. 2019, 13 pages.
Zhang, et al., "Skin Delivery of Hydrophilic Biomacromolecules Using Marine sponge spicules", pubs.acs.org/molecularpharmaceutics, 2017, pp. 3188-3200.
Mitragotri, et al., "Low-frequency sonophoresis A review", Advanced Drug Delivery Reviews 56 (2004) 589-601, 13 pages.

* cited by examiner

*Primary Examiner* — Craig D Ricci
*Assistant Examiner* — Paul Hoerner
(74) *Attorney, Agent, or Firm* — Cooper Legal Group, LLC

(57) ABSTRACT

A drug transdermal delivery system comprises sponge spicules and a low-frequency sonophoresis device, the drug transdermal delivery system firstly applies a low-frequency sonophoresis to skin using the low-frequency sonophoresis device, a surface of the skin is then massaged with the sponge spicules.

7 Claims, 6 Drawing Sheets

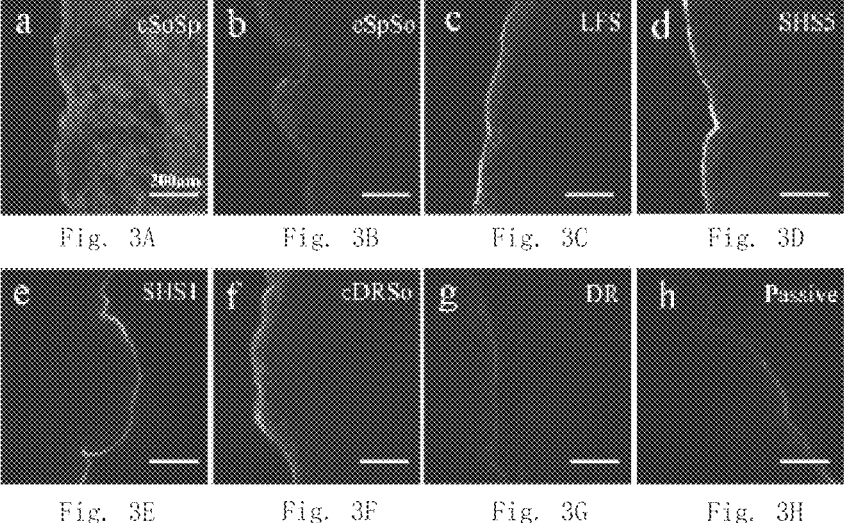
Fig. 3A      Fig. 3B      Fig. 3C      Fig. 3D
Fig. 3E      Fig. 3F      Fig. 3G      Fig. 3H
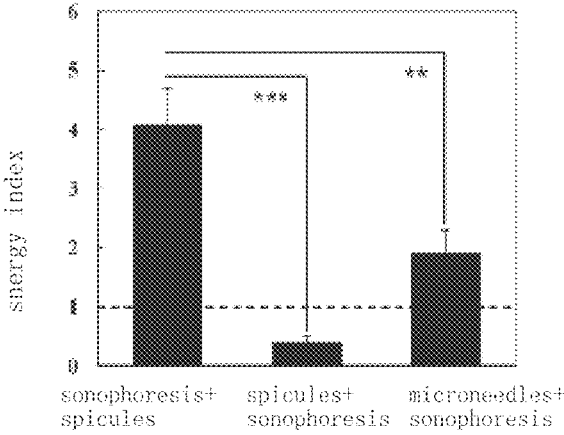
Fig. 4

DRUG TRANSDERMAL DELIVERY SYSTEM

RELATED APPLICATIONS

This application is a continuation of International patent application PCT/CN2020/101041, filed on Jul. 9, 2020, which claims priority to Chinese patent application 201910619867.8, filed on Jul. 10, 2019. International patent application PCT/CN2020/101041 and Chinese patent application 201910619867.8 are incorporated herein by reference.

FIELD OF THE DISCLOSURE

The present disclosure relates to a drug transdermal delivery system and a method thereof.

BACKGROUND OF THE DISCLOSURE

Skin Drug Delivery has many unique advantages compared with other routes of administration, including: avoiding the first pass effect of the liver; drug absorption not being affected by the digestive tract environment and gastrointestinal function; sustained or controlled drug delivery; good patient compliance; and among others. However, the essence of the skin is a biological membrane barrier. Except for a very small number of drug molecules (with molecular weights less than 500 Da and moderate oil-water partition coefficients) that can pass through the stratum corneum barrier, most drug molecules have difficulty penetrating and being absorbed through the skin. Therefore, it is a challenging task to overcome the skin barrier and safely and effectively deliver various biomacromolecule drugs or active substances with different physical and chemical properties to a lesion through skin, and it has also been a research challenge and hot spot in the field of skin drug delivery.

Among all transdermal delivery technologies, microneedle technology is the most promising. Since its introduction in 1998, microneedle technology has gradually developed five categories, including solid microneedles, hollow microneedles, dissolving microneedles, coated microneedles, and phase-transition microneedles. They are mainly used for vaccination, insulin administration, and the treatment of skin diseases and others. However, microneedle technology still faces a series of challenges and bottlenecks in the treatment of skin diseases, including: the maintenance time of the micropores induced by the solid microneedle is too short, and the microchannel usually closes automatically within 20 minutes after the microneedle leaves the skin, which greatly limits the transdermal penetration and bioavailability of the drug. The administration area of microneedle patches (including dissolving microneedles, coated microneedles, hollow microneedles, etc.) is fixed and relatively small (usually 1 cm$^2$), which limits the use of the microneedle patches to the treatment of large-area skin lesions. Microneedles are usually arranged in an array, and it is difficult for the microneedle patches to be applied on different surfaces and uneven areas such as the alar of the nose.

The applicant separated and purified the sponge spicule of *Haliclona* sp. (SHS) from artificially cultivated *Haliclona* sp., which had sharp ends, stable properties, and high mechanical strength (the content of SiO$_2$ is 95%), the sponge spicule of *Haliclona* sp. has a unified shape and is uniform in size (the sponge spicule of *Haliclona* sp. is about 120 μm in length and is about 7 μm in diameter). The sponge spicule of *Haliclona* sp. can be used as a microneedle technology to be applied to the skin to effectively promote the transdermal delivery of model drugs (S. Zhang, et al., 2017) and nano-carriers (C. Zhang, et al., 2019). The efficiency of SHS to deliver model drugs (e.g., dextran, which has a molecular weight of 10 kDa) on the skin of living mice is about 15 times that of commercial solid microneedles (Dermaroller® 200 μm). However, the use of SHS for skin administration still has many shortcomings, including: 1) the penetration enhancement effect of SHS decreases sharply with the increase of the molecular weight of the drug; and 2) the skin irritation of SHS is related to its dosage. The greater the dosage, the greater the massage intensity and the greater the skin irritation.

Low-frequency sonophoresis acts on the skin to produce powerful cavitation. The vibration of cavitation bubbles at an interface of the keratinocyte-lipid molecule layer causes the vibration of the lipid bilayer of the stratum corneum of the skin, resulting in disordered arrangement of lipids in the stratum corneum. At the same time, shockwaves generated by the rupture of cavitation bubbles at the interface also contributes to the disordered arrangement of lipids in the stratum corneum and can induce a large number of microjets to form drug penetration pores on the skin surface. The vibration of the cavitation bubbles can take a large amount of water to penetrate into the disordered lipid area to form an aqueous channel and open the stratum corneum barrier. Low-frequency sonophoresis does not damage the protective properties of the skin and the subcutaneous muscle tissue. Low-frequency sonophoresis can improve the permeability of the skin and allow drug molecules to penetrate the skin. It is a potential alternative to the traditional route of administration. Low-frequency sonophoresis enables controlled administration of treatments such as insulin, interferon, erythropoietin, etc. However, the transdermal delivery efficiency of low-frequency sonophoresis for macromolecular drugs is not high. The low transdermal delivery efficiency is caused by the inhomogeneous penetration area formed by the low-frequency sonophoresis on the skin. Additionally, due to safety considerations, an output energy of low-frequency sonophoresis during actual clinical use is lower and the action time is shorter.

BRIEF SUMMARY OF THE DISCLOSURE

The present disclosure provides a drug transdermal delivery system.

In order solve the technical problems, a technical solution of the present disclosure is as follows.

A drug transdermal delivery system comprises sponge spicules and a low-frequency sonophoresis device, the drug transdermal delivery system firstly applies a low-frequency sonophoresis to skin using the low-frequency sonophoresis device, a surface of the skin is then massaged with the sponge spicules, and a drug is then administered or applied to the surface of the skin; or after the drug transdermal delivery system applies the low-frequency sonophoresis to the skin using the low-frequency sonophoresis device: the surface of the skin is massaged with the sponge spicules, and the drug is administered or applied to the surface of the skin at the same time as the surface of the skin is massaged with the sponge spicules.

In an embodiment, the sponge spicules are sponge spicules of *Haliclona* sp.

In an embodiment of the present disclosure, a frequency of the low-frequency sonophoresis is 10-30 kHZ.

In an embodiment of the present disclosure, the frequency of the low-frequency sonophoresis is 15-28 kHZ.

In an embodiment of the present disclosure, an output power for the low-frequency sonophoresis is 5-7 W/cm$^2$, and skin irritation is reduced.

In an embodiment of the present disclosure, a time for the low-frequency sonophoresis is applied for 2 minutes or less, and the skin irritation is reduced.

In an embodiment of the present disclosure, a dosage amount of the sponge spicules is 1 mg/cm$^2$ or less, and the skin irritation is reduced.

Compared with the existing techniques, the present disclosure has the following advantages.

1. A synergistic penetration enhancement system using sponge spicules and a low-frequency sonophoresis can significantly enhance the permeability of skin to hydrophilic drug molecules. Compared with the use of low-frequency sonophoresis alone for penetration enhancing or the use of sponge spicules alone for penetration enhancing, the penetration enhancing effect from the combination of the two technologies is significantly enhanced. Low-frequency sonophoresis will form shockwaves and liquid microjets when acting on a surface of the skin. The shockwaves will loosen the structure of the stratum corneum, while the liquid microjets will form some 1-2 μm diameter microchannels on the stratum corneum. However, the distribution of these microchannels on the surface of the skin is not homogeneous, the number of microchannels is limited, and the efficiency of drug molecules entering the stratum corneum is not high and is inhomogeneous, so the delivery effect of drug molecules is not significant, and the effect of sonophoresis is not significant. The skin treated with the sonophoresis is then massaged with sponge spicules. After the sponge spicules penetrates into the stratum corneum of the skin, the sponge spicules form a large number of new pores in the stratum corneum (1 mg/cm$^2$ of sponge spicules can produce 674±129/mm$^2$ microchannels), so that the drug or active ingredient can take full advantage of the loose structure of the stratum corneum caused by the previous sonophoresis shockwave, so that a large number of drugs or active ingredient molecules enter and break through the stratum corneum barrier and smoothly enter the deep layers of the skin. The synergistic promotion effect of the two technologies is significantly enhanced.

2. Comparison with traditional microneedle technology: compared with a microneedle roller, the sponge spicules of *Haliclona* sp. can penetrate the stratum corneum to open the skin barrier and stay in the stratum corneum for a long time to form a large number of persistent microchannels (at least 72 hours). It is much longer than the residence time of the microchannel after the traditional microneedles act on the skin (20 minutes), so it is more helpful for the drug to continuously penetrate into the skin. Compared with the microneedle patch, the sponge spicules of *Haliclona* sp. can be used in any area and any non-flat skin lesions, so it is more convenient to use.

3. Comparison of the synergy of the sponge spicules of *Haliclona* sp. and the low-frequency sonophoresis with the synergy of the traditional microneedles and the low-frequency sonophoresis: the low-frequency sonophoresis forms a small number of microchannels on the surface of the skin, but the number of microchannels formed by the sponge spicules of *Haliclona* sp. on the surface of the skin is very large. A dosage amount of 1 mg/cm$^2$ of the sponge spicules can produce 674±129 microchannels/mm$^2$), which can fully play a synergistic effect. In contrast, traditional microneedles, such as the microneedle roller, form a small amount of microchannels on the surface of the skin, and the synergy between the two is not significant. The transdermal delivery efficiency for drugs is far lower than the synergistic combination of the sonophoresis and the sponge spicules, so the sponge spicules of *Haliclona* sp. can be a good substitute for traditional microneedles and to be combined with the low-frequency sonophoresis to perform better.

4. The synergistic penetration enhancement system of the sponge spicules of *Haliclona* sp. and the low-frequency sonophoresis can reduce the dosage amount and massage intensity of the sponge spicules of *Haliclona* sp., reduce the skin irritation of the sponge spicules of *Haliclona* sp., and effectively increase the safety of use.

5. As a new type of drug transdermal delivery method, the drug transdermal delivery method can effectively deliver the low-molecular-weight heparin percutaneously into the deep layers of the skin and subcutaneous capillaries, and reach the body through the blood circulation. The drug transdermal delivery method has a good effect on superficial venous thrombus and even deep venous thrombus. The therapeutic effect provides a good treatment method for clinical treatment of venous thrombus in the future.

BRIEF DESCRIPTION OF THE DRAWINGS

The present disclosure will be further described in combination with the accompanying embodiments and drawings.

FIGS. 3A-3H illustrate fluorescence distributions of a model drug in the various skin layers.

FIG. 4 illustrates an analysis diagram of synergistic coefficients using various synergistic administration methods.

DETAILED DESCRIPTION OF THE EMBODIMENTS

Figure 1:
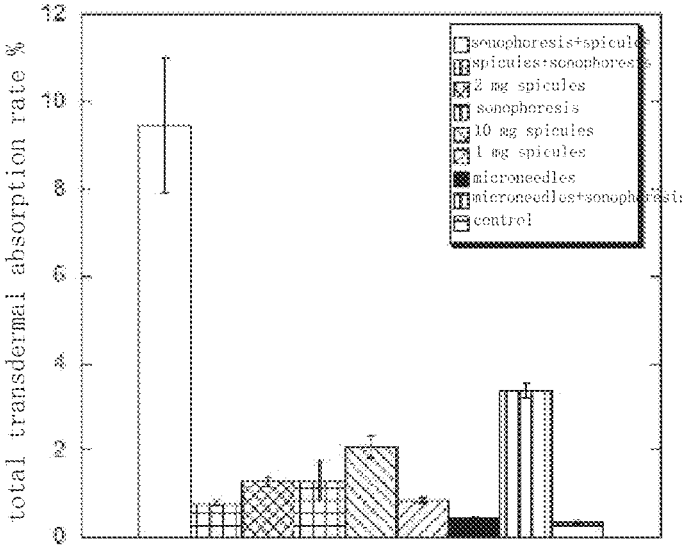
FIG. 1 illustrates a total transdermal absorption of FITC-Dextran-4K (FD-4K) using various transdermal delivery methods.
Figure 2:
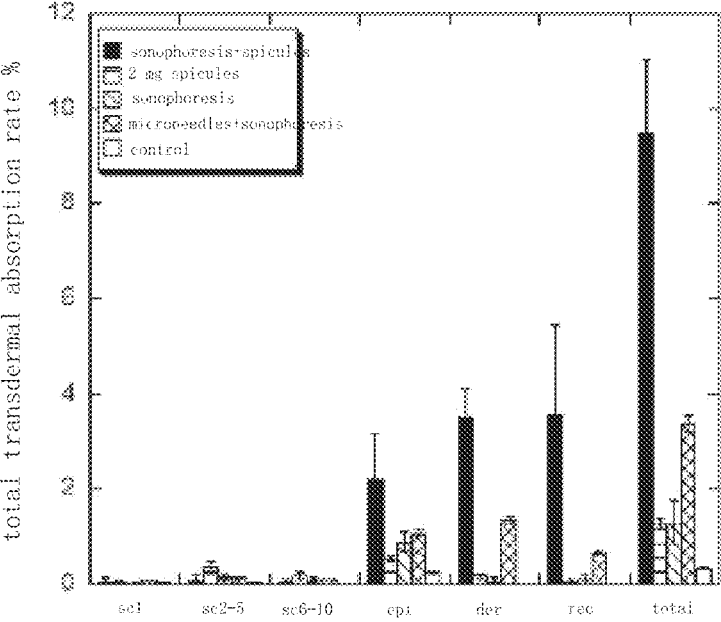
FIG. 2 illustrates an accumulated distribution of FD-4K in various skin layers using the various transdermal delivery methods, wherein SC1-10 represents 1$^{st}$-10$^{th}$ layers of stratum corneum along an inward direction (which is separated by a tape peeling method), Epi represents an active epidermal layer, Der represents a dermis layer, and Rec represents a receptor compartment.

An experimental basis for the embodiments of the present disclosure is as follows:

1. Sponge spicules of *Haliclona* sp.: a preparation method of the sponge spicules of *Haliclona* sp. may be found in CN201610267764.6, "A method for preparing sponge spicules with a high purity", which is incorporated herein by reference.

2. A sonophoresis device: a JY-92IIN sonophoresis cell disrupter from Ningbo Scientz Biotechnology Co., Ltd. Parameters of the sonophoresis cell disrupter are as follows:

a. An sonophoresis frequency: 20 kHZ;

b. A total time for sonophoresis: 30 seconds (a working ratio is 50%, a turn-on time for the sonophoresis is 2 seconds, and a turn-off time for the sonophoresis is 2 seconds);

c. Thermodynamic parameters of an output power for the sonophoresis: 6.8 W/cm$^2$;

d. Coupling medium for the sonophoresis: 2 mL of 1% sodium lauryl sulfate (SLS) (which is dissolved in 0.2 mol/L phosphate buffered saline (PBS) buffer solution); and e. A distance between an amplitude converter and skin: 10 mm.

3. A model drug: fluorescently labeled dextran (a molecular weight of the dextran is 4000, FD-4K, a concentration of the dextran is 1 mg/mL).

4. A therapeutic drug: a low-molecular-weight heparin (dalteparin).

Embodiment 1—An Experiment In Vitro

A circular isolated porcine skin with a diameter of 2 cm and a lipophilic layer removed without damage to layers of the stratum corneum is fixed on a Franz diffusion cell, 12 mL of 0.2 mol/L PBS buffer solution is added into a receptor compartment, and the porcine skin is clamped with a clamp to perform a-e groups using topical administration.

a. A group using the sonophoresis and then using the spicules: the porcine skin in the Franz diffusion cell is treated with low-frequency sonophoresis for 120 seconds (see the aforementioned section of the parameters of the sonophoresis device), and a solution of a coupling agent in a donor compartment is then sucked out, the porcine skin is washed with 0.2 mol/L PBS buffer solution for three times, 100 μL of a solution of the sponge spicules of *Haliclona* sp. with a concentration of 20 mg/mL is added into the donor compartment, and the porcine skin is then manually massaged for 2 minutes (a revolution speed is 120 r/min), the residual solution of the sponge spicules of *Haliclona* sp. is washed away, 150 μL of the model drug is added, and the transdermal delivery in vitro is started.

b. A group using the spicules and then using the sonophoresis: 100 μL of a solution of the sponge spicules of *Haliclona* sp. with a concentration of 20 mg/mL is added into the donor compartment of the Franz diffusion cell, and the porcine skin is then manually massaged for 2 minutes (a revolution speed is 120 r/min), the residual solution of the sponge spicules of *Haliclona* sp. is then washed away, the porcine skin is treated with low-frequency sonophoresis for 120 seconds (which is the same as the group a), a solution of the coupling agent in the donor compartment is then sucked out, the porcine skin is washed with 0.2 mol/L PBS buffer solution for three times, 150 μL of the model drug is then added, and the transdermal delivery in vitro is started.

c. A massage group using various dosage amounts of the sponge spicules of *Haliclona* sp.: 100 μL of solutions of the sponge spicules of *Haliclona* sp. with concentrations of 20 mg/mL, 100 mg/mL, and 10 mg/mL are added into the donor compartment of Franz diffusion cell, the porcine skin is then manually massaged for 2 minutes (a revolution speed is 120 r/min), the residual solutions of the sponge spicules of *Haliclona* sp. are then washed away, 150 μL of the model drug is respectively added, and the transdermal delivery in vitro is started.

d. A sonophoresis group: the porcine skin in the Franz diffusion cell is treated with the low-frequency sonophoresis for 120 seconds (which is the same as the steps of the technical solution), and a solution of the coupling agent in the donor compartment is then sucked out, the porcine skin is washed for three times with 0.2 mol/L PBS buffer solution, 150 μL of the model drug is then added, and the transdermal delivery in vitro is started.

e. A control group: without any treatment, 150 μL of the model drug is added into the donor compartment, and the transdermal delivery in vitro is started.

A pretreatment using microneedles: a circular isolated porcine skin with a diameter of 2 cm and without damage to layers of the stratum corneum, a lipophilic layer below the dermis layer is removed, a microneedle roller (e.g., German Dermaroller) (a length of microneedles is 0.2 mm, a number of the microneedles is 162) is used to roll on a surface of a skin for one time along a "✳" shape, and the porcine skin pretreated by the microneedles is fixed on the Franz diffusion cell.

f. A microneedle group: 150 μL of the model drug is added to porcine skin pretreated by the microneedles, and the transdermal delivery in vitro is started.

g. A group using the microneedles combined with the sonophoresis: the porcine skin pretreated with the microneedles in the Franz diffusion cell is treated with the low-frequency sonophoresis for 120 seconds (which is the same as the steps of the technical solution), a solution of the coupling agent in the donor compartment is sucked out, and the porcine skin is washed for three times with 0.2 mol/L PBS buffer solution, 150 μL of the model drug is added, and the transdermal delivery in vitro is started.

Scanning electron microscopy analysis for nude mouse skin: scanning electron micrographs of the nude mouse skin topically pretreated by four groups, including the control group, the sonophoresis group, the group using the spicules and then using the sonophoresis, and the group using the sonophoresis and then using the spicules (the method is the same as the aforementioned method) are taken to analyze morphologies and microstructures of a surface of the skin.

Staining of topical penetration sites of the skin: the nude mouse skin topically pretreated by three groups, including the sonophoresis group, the 2 mg spicule group, and the group using sonophoresis and then using the spicules (the method is the same as the aforementioned method), a gentian violet solution is added into the donor compartment, stained for 24 hours, and washed by an ethanol solution, and the residue liquid on the surface is absorbed with absorbent paper, a penetration situation of a surface of the stratum corneum layer for the staining solution is observed, the stratum corneum layer and the epidermal layer of the skin are then scrapped by a blade, and a penetration situation of the dermis layer for the staining solution is observed. Results:

1. After the transdermal delivery in vitro is applied for 16 hours using the various topical drug administration methods of the groups a-g and is isolated using the tape stripping method, drug contents of each skin layer is analyzed, transdermal absorption effects are compared, and the results are shown in FIG. 1. Distribution states of FD-4K in various layers of the skin are compared, and the results are shown in FIGS. 2 and 3A-3I. Synergy index of the transdermal delivery using various synergistic administration methods are analyzed, and the results are shown in FIG. 4.

2. After the transdermal delivery in vitro is applied for 16 hours using the various topical drug administration methods, skin tissue is sliced into slices with a thickness of 20 μL using a cryostat microtome. After the slices are fixed and mounted using a resin, a laser confocal microscope (an excitation wavelength is 490 nm, and an emission wavelength is 530 nm) is used to observe distribution states of drug fluorescence in the various layers of the skin, and the results are shown in FIGS. 3A-3I. FIG. 3A illustrates the transdermal delivery using the sonophoresis and then using the 2 mg spicules (cSoSp), FIG. 3B illustrates the transdermal delivery using the 2 mg spicules and then using the sonophoresis (cSpSo), FIG. 3C illustrates the transdermal delivery using the sonophoresis (LFS), FIG. 3D illustrates the transdermal delivery using the 10 mg spicules (SHS5), FIG. 3E illustrates the transdermal delivery using the 2 mg spicules (SHS1), FIG. 3E illustrates the transdermal delivery using the microneedles and then using the sonophoresis (CDRSo), FIG. 3F illustrates the transdermal delivery using the microneedles (DR), and FIG. 3H illustrates the control group (passive).

Figures 5A, 5B, 5C, 5D, 6A, 6B, 6C, 6D, 6E, 6F:
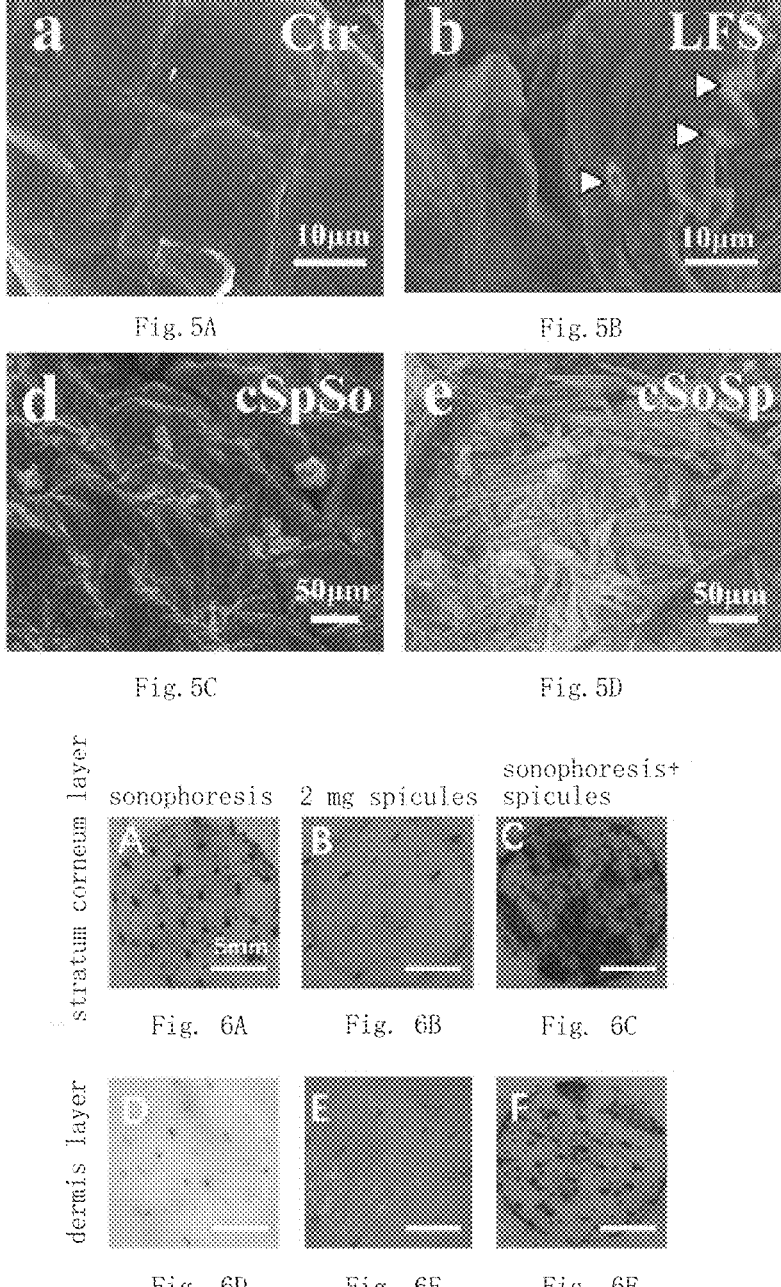
FIGS. 5A-5D illustrate scanning electron microscopes of guinea pig skin.
FIGS. 6A-6F illustrate staining diagrams of penetration sites of porcine skin.

3. According to the results of the scanning electron microscopy analysis of FIGS. 5A-5D, compared with a flat skin surface of the control group (see FIG. 5A), the surface of the nude mouse skin will generate an aperture larger than 2 μm by the sonophoresis (see FIG. 5B). A large number of the spicules pierce into the surface of the guinea pig skin (1 mg/cm$^2$ of sponge spicules can generate 674±129 microchannels/mm$^2$, see FIG. 5D) using the sonophoresis and then using the 2 mg spicules, which is far higher than the number of residue spicules of the surface of the skin of the guinea pig using the 2 mg spicules and then using the sonophoresis (approximately 162±91 microchannels/mm$^2$, see FIG. 5C). FIG. 5A illustrates the control group (Ctr), FIG. 5B illustrates the transdermal delivery using the sonophoresis (LFS), FIG. 5C illustrates the transdermal delivery using the 2 mg spicules and then using the sonophoresis (cSpSo), and FIG. 5D illustrates the transdermal delivery using the sonophoresis and then using the 2 mg spicules (cSoSp).

4. According to staining diagrams of penetration sites of the skin of FIGS. 6A-6F, the synergistic effect of the sonophoresis and the spicules enable the surface of the skin to generate a plurality of penetration channels, so that the staining solution can infiltrate the plurality of penetration channels (see FIG. 6A), which is much higher than using the sonophoresis alone or using the spicules alone (See FIGS. 6B and 6C), and scales of the plurality of penetration channels are deeper. Even after the stratum corneum and the epidermal layer are scraped off, a large amount of the staining solution can still infiltrate into the dermis layer (see FIG. 6F), it is difficult for the staining solution to infiltrate into a deep position of the skin using the sonophoresis alone or using the spicules alone, and there is almost no residue staining solution in the dermis layer (see FIGS. 6D and 6E).

The following results are obtain from an analysis of the quantitative results and the qualitative results.

1) The synergistic effect of the low-frequency sonophoresis and the sponge spicules of *Haliclona* sp. can significantly enhance a transdermal delivery rate (9.5±1.6%) of FD-4K dextran, which is much greater than a transdermal delivery rate using the sponge spicules of *Haliclona* sp. alone (1.3±0.1%) or using the low frequency sonophoresis alone (1.3±0.5%) and is also significantly higher than a transdermal delivery rate using the microneedle roller (0.5±0.1%) or synergistically using the microneedle roller and the low-frequency sonophoresis (3.4±0.2%).

2) After the skin is processed synergistically using the low-frequency sonophoresis and the sponge spicules of *Haliclona* sp., most drug molecules are accumulated in a deep skin layer below the epidermal layer and completely pass through the stratum corneum barrier. In contrast, the drug has difficulty mostly passing through the stratum corneum barrier using other drug transdermal delivery methods, and the drug is mostly accumulated above the epidermal layer and blocked by the stratum corneum.

3) When the skin treated using the sponge spicules is compared with the skin treated using the sonophoresis, the drug is easily delivered to an active epidermal layer when the skin treated using the sponge spicules, which indicates that a function depth of the low-frequency sonophoresis is deeper than that of the sponge spicules with respect to the skin surface.

4) When the synergistic coefficients of the various synergistic delivery methods are compared and analyzed, the synergistic effect for using the sonophoresis and then using the spicules (4.1±0.6) is better than the synergistic effect for using the microneedles and then using the sonophoresis (1.9±0.4, p<0.01) and the synergistic effect for using the spicules and then using the sonophoresis (0.4±0.1, p<0.001). Therefore, the synergy for using the sonophoresis and then using the spicules is an optimal synergy with respect to the transdermal delivery cooperative effect.

5) A sequence for using the sonophoresis and the spicules effectively influences the effects. The skin should be firstly treated with the low-frequency sonophoresis, the sponge spicules of *Haliclona* sp. are then used to massage the surface of the skin, and the cooperative effect of the low-frequency sonophoresis and the sponge spicules is achieved. On the contrary, the synergistic effect of firstly using the spicules for massaging the surface of the skin and then using the low-frequency sonophoresis to treat the skin is not obvious, and a drug transdermal delivery rate is not high. Reasons and possible mechanisms are analyzed as follows.

(1) With respect to synergistically using the spicules and then using the sonophoresis: a pretreatment of the sponge spicules of *Haliclona* sp. will open the stratum corneum barrier, and a large number of spicules pierce into the surface of the skin, and the low-frequency sonophoresis is then used to provide energy to a coupling medium (e.g., the coupling agent) to induce acoustic cavitation, resulting in bubbles generated in the coupling medium growing rapidly and breaking. However, as the large number of spicules with low weights and small volumes are accumulated on the surface of the skin, break processes of cavitation bubbles generated in the coupling medium on the surface of the skin will also be blocked by the spicules on the surface of the skin, resulting in liquid microjets functioning to increase the sonophoresis penetration rate being blocked. Therefore, hydrophilic channels are significantly reduced. Additionally, the cavitation bubbles on the surface of the skin break, and the sponge spicules of *Haliclona* sp. piercing into the skin are significantly shed, so that penetration enhancement effect of the sponge spicules of *Haliclona* sp. is weakened, which is not helpful for the drug molecules continuously penetrating into the skin at a later stage.

(2) With respect to synergistically using the sonophoresis and then using the spicules: the low-frequency sonophoresis is used to provide energy to a coupling medium to induce acoustic cavitation, resulting in bubbles generated in the coupling medium growing rapidly and breaking. The bubbles are broken on the surface of the skin to generate liquid microjets, so that some hydrophilic channels that are inhomogeneously distributed are generated. Further, sonophoresis energy is transmitted to the surface of the skin to reduce cavitation functions in the lipophilic layer of the skin, a molecular arrangement of the lipophilic layer of the stratum corneum is changed to enable the molecular arrangement to become loose, the sponge spicules then pierce the stratum corneum of the skin using massage, and the skin barrier is then fully opened. Loose effect of the stratum corneum structure induced by the sonophoresis is effectively utilized, the synergistic delivery effect for using the low-frequency sonophoresis and then using the sponge spicules of *Haliclona* sp. is maximized, and it helps the drug molecules to penetrate into the skin.

Therefore, when the skin is pretreated using the sonophoresis and then massaged using the sponge spicules of *Haliclona* sp., a delivery efficiency of the drug molecules is significantly improved.

Embodiment 2—Experiments In Vivo

A transdermal delivery of low-molecular-weight heparin is used to treat superficial venous thrombus using a synergistic system using the sonophoresis and then using the spicules.

An experimental method:

A topical injection of thrombin is used to establish an animal model of a rabbit ear thrombus: hair of an ear of the New Zealand rabbit is carefully shaven off, a blood vessel section from an external ear vein with a length of about 2 cm and having fewer branches is selected, 40 U of the thrombin is injected into the blood vessel section, and a hemostatic clip is used to block a blood flow of the blood vessel section at a proximal end of a heart. After 2 hours, the blood is completely coagulated to form a venous thrombus, and the hemostatic clip is then loosen. A length of the venous thrombus is measured and recorded, and the rabbit ear successfully modeled is sliced into a slice by the cryostat microtome. After the slice is stained by a hematoxylin and eosin (HE) tissue staining method and fixed by the resin, and the slice is mounted for observation.

With respect to the various administration methods, the rabbits successfully modeled are divided into a therapy group for a proximal venous thrombus and a therapy group for a distal venous thrombus, and the rabbits are topically treated by the low-molecular-weight heparin (300 U/kg rabbit body weight) for therapy. With respect to the therapy group for the proximal venous thrombus, the low-molecular-weight heparin is administered using four topical administration methods after the ear thrombus on a side of the ear modeled is pretreated, respectively namely: a. a smear group; b. a 2 mg spicules group; c. an sonophoresis group; and d. a group using the sonophoresis and then using the spicules. With respect to the therapy group for the distal venous thrombus, the low-molecular-weight heparin is administered using two topical administration methods after a blood vessel on a side of the ear unmodeled is pretreated, respectively namely: a. a group using the sonophoresis and then using the spicules and b. an intravenous injection group. A pretreatment method is the same as described with respect to in vitro.

Figure 7:
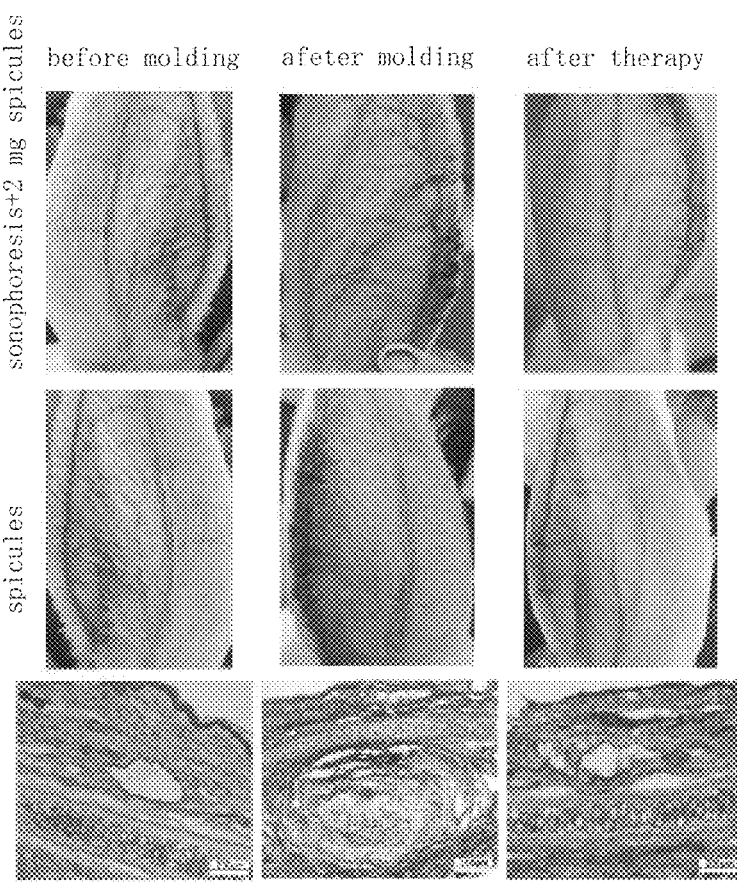
FIG. 7 illustrates a diagram of a therapeutic slice of a rabbit ear thrombus model.

Results:

1. FIG. 7 illustrates the modeled results of the rabbit ear thrombus. A blood flow of a normal rabbit ear is unobstructed and red, and no thrombus exists in the vessel. After the thrombin is injected to be molded, black strip-shaped thrombus appears in the blood vessel, and the blood vessel is blocked by the thrombus. After the low-molecular-weight heparin is delivered and is treated for 48 hours synergistically using the sonophoresis and then using the spicules, the black strip-shaped thrombus in the blood vessel is almost completely dissolved, and the blood vessel returns to an original state. However, after the low-molecular-weight heparin is delivered and is treated for 48 hours using the spicules alone, the thrombus is not completely dissolved and partially blocks the blood vessel.

Figure 8A:
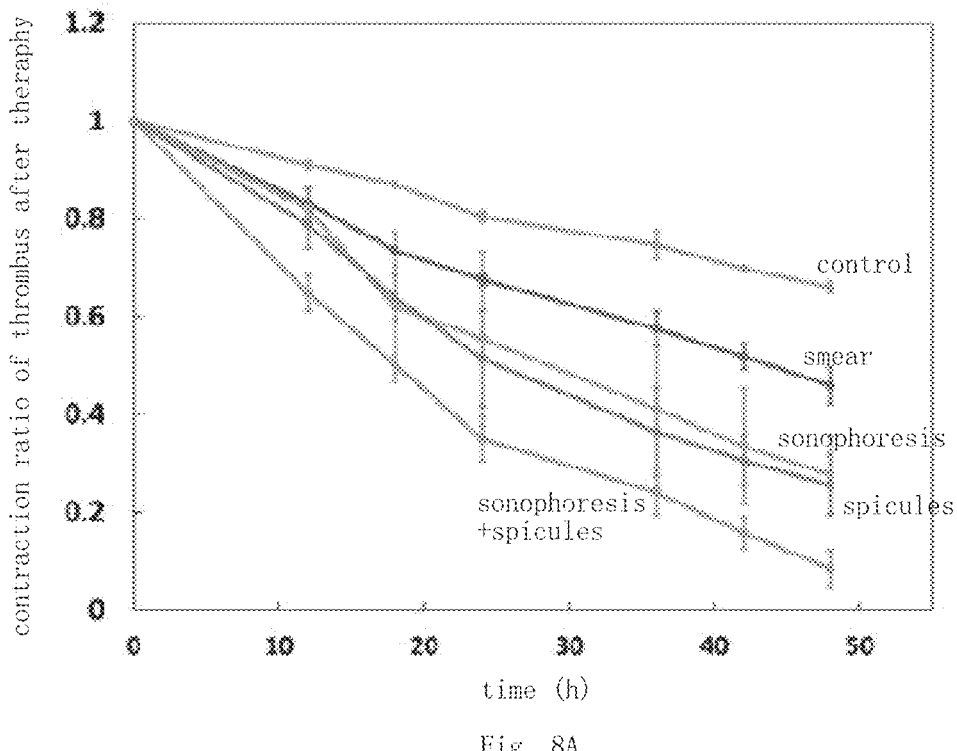
FIGS. 8A and 8B illustrate statistical charts of therapeutic effects for a venous thrombus.
Figure 8B:
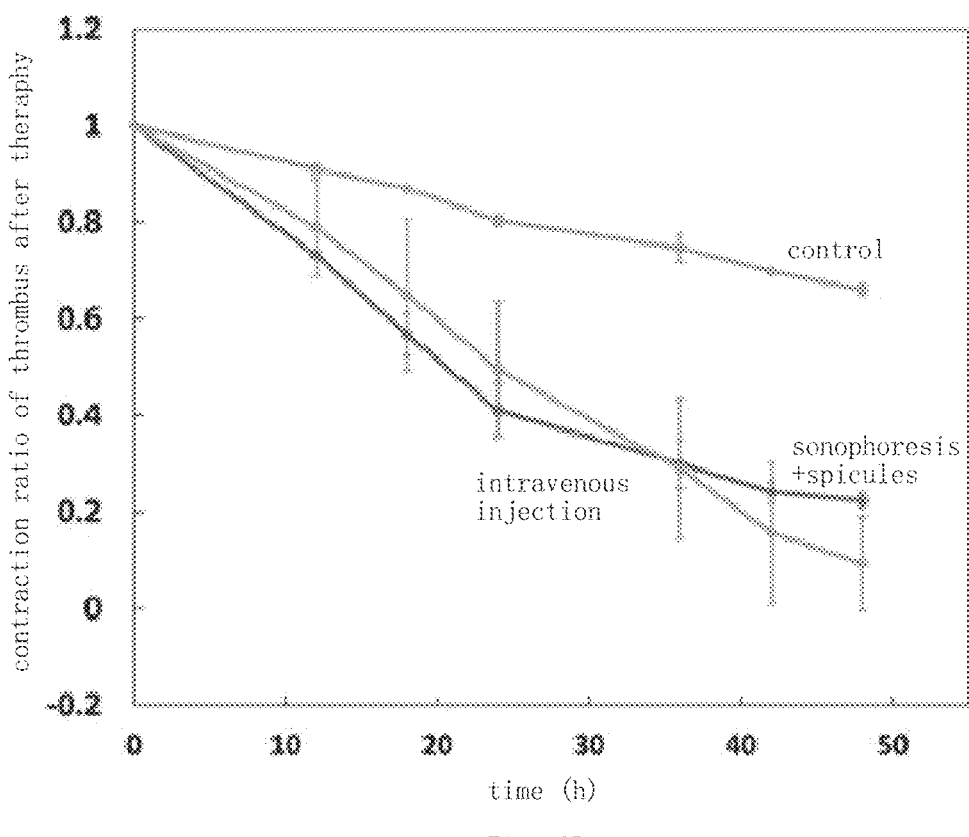

2. FIGS. 8A and 8B illustrate a measurement, a statistic, and an analysis of thrombus length variations before treatment and after treatment in each group. Referring to FIG. 8A, with respect to the therapy group for the proximal venous thrombus, after delivering the low-molecular-weight heparin synergistically using the sonophoresis and then using the spicules for 48 hours of therapy, the thrombus is basically dissolved, which is better than other groups. Referring to FIG. 8B, with respect to the therapy group for the distal venous thrombus, compared with using intravenous injection, there is no significant difference for thrombus dissolvability degrees after the low-molecular-weight heparin is delivered and is treated for 48 hours at a distal end using the sonophoresis and then using the spicules, which indicates that the low-molecular-weight heparin can be successfully delivered into the blood circulation using the delivery method.

With respect to the therapy results of the rabbit ear thrombus:

The low-molecular-weight heparin can be successfully delivered into subcutaneous tissues to successfully treat the venous thrombus due to the synergistic effect for using the sonophoresis and then using the spicules and enters into the body following the blood circulation. The low-molecular-weight heparin also has a good therapeutic effect with respect to the distal venous thrombus, which indicates an effectiveness of the synergistic system.

Figure 9:
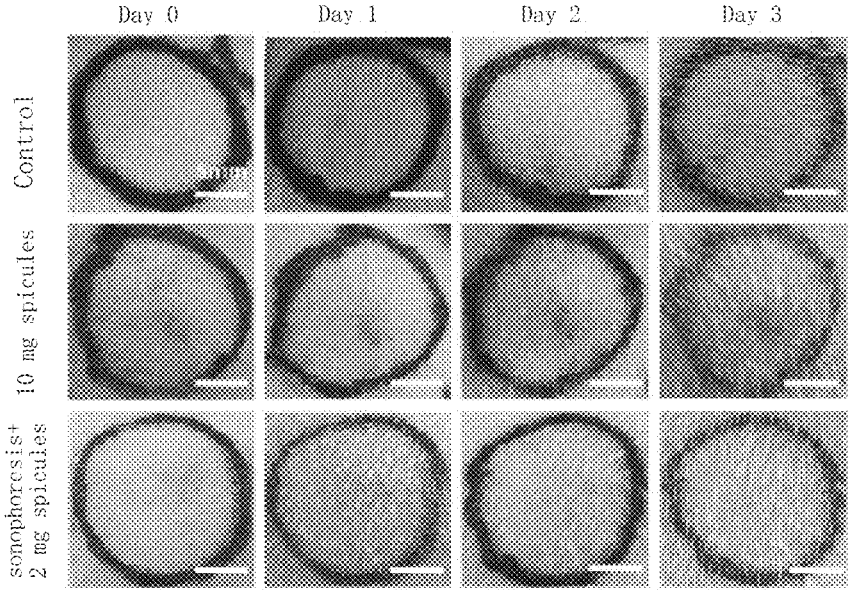
FIG. 9 illustrates a safety data sheet of a synergistic use of low-frequency sonophoresis and spicules.

The safety of the technology using the low frequency sonophoresis and then using the sponge spicules of *Haliclona* sp.:

1) An Experimental Method:

8-10 week old, ordinary female guinea pigs are selected, hair of a surface of a rear flat skin of the ordinary female guinea pig is shaved off without destroying an integrity of the skin of the ordinary female guinea pig, an experimental section with a diameter of 15 mm is circled, a control group and two experimental groups (which are respectively a 10 mg spicules group and a group using the sonophoresis and then using 2 mg spicules, the experimental method is the same as the aforementioned content) are arranged. Referring to FIG. 9, irritation states of the surface of the skin of the ordinary female guinea pig using various administration methods within 72 hours are recorded and observed.

2) Experimental Results:

According to Draize skin irritation evaluation standard and Primary Irritation Index (PII) (main irritation index, 0-0.4 represents no irritation, and 0.5-1.9 represents mild irritation) which are internationally accepted, erythema states and edema states of the skin are compared analyzed after each experimental group is complete. The synergistic group using the sonophoresis and then using the 2 mg spicules (PII=0.64) has lower skin irritation than the group using the 10 mg spicules alone (PII=1.61), which indicates that the synergistic system using the low-frequency sonophoresis and then using the sponge spicules of *Haliclona* sp. has less irritation relative to the skin and effectively increases the safety of use. The synergistic group using the sonophoresis and then using the 2 mg spicules can significantly reduce a dosage amount and a massage intensity of the sponge spicules of *Haliclona* sp., thereby the skin irritation is greatly reduced.

The aforementioned embodiments are merely some embodiments of the present disclosure, and the scope of the disclosure of is not limited thereto. Thus, it is intended that the present disclosure cover any modifications and variations of the presently presented embodiments provided they are made without departing from the appended claims and the specification of the present disclosure.

What is claimed is:

1. A drug transdermal delivery method, comprising:
operations of:
firstly applying a low-frequency sonophoresis to skin, wherein a frequency of the low-frequency sonophoresis is 10-30 kHZ, and a time during which the low-frequency sonophoresis is applied is 2 minutes or less,
then massaging a surface of the skin with sponge spicules for 2 minutes, wherein a dosage amount of the sponge spicules is 1 mg/cm$^2$ or less, and
then administering a drug to the surface of the skin; or operations of:
firstly applying the low-frequency sonophoresis on the skin, wherein the frequency of the low-frequency sonophoresis is 10-30 kHZ, and the time during which the low-frequency sonophoresis is applied is 2 minutes or less,
then massaging the surface of the skin using the sponge spicules for 2 minutes, wherein the dosage amount of the sponge spicules is 1 mg/cm$^2$ or less, and
administering the drug to the surface of the skin at the same time as the surface of the skin is massaged using the sponge spicules.

2. The method according to claim 1, comprising:
cleaning the skin before administrating the drug to the surface of the skin.

3. The method according to claim 1, comprising:
administering the drug within 72 hours after applying the low-frequency sonophoresis to the skin and then massaging the surface of the skin with the sponge spicules.

4. The method according to claim 1, wherein an output power for the low-frequency sonophoresis is 5-7 W/cm$^2$.

5. The method according to claim 1, wherein the sponge spicules are sponge spicules of *Haliclona* sp.

6. The method according to claim 1, wherein the frequency of the low-frequency sonophoresis is 15-28 kHZ.

7. The method according to claim 1, wherein:
the time during which the low-frequency sonophoresis is applied is 2 minutes, and
massaging the surface of the skin with the sponge spicules comprises applying a solution of the sponge spicules with a concentration of 20 mg per mL of the solution.

\* \* \* \* \*